United States Patent [19]
Harris

[11] Patent Number: 6,133,261
[45] Date of Patent: Oct. 17, 2000

[54] AMINO ACID DERIVATIVES USEFUL TO TREAT STROKE

[75] Inventor: Robert H. Harris, Holmdel, N.J.

[73] Assignee: Research Corporation Technologies, Inc., Tucson, Ariz.

[21] Appl. No.: 09/116,071

[22] Filed: Jul. 15, 1998

Related U.S. Application Data

[60] Provisional application No. 60/052,684, Jul. 15, 1997.

[51] Int. Cl.$^7$ .......................... A61K 31/445; A61K 31/34
[52] U.S. Cl. ....................... 514/231.2; 514/315; 514/357; 514/397; 514/406; 514/415; 514/424; 514/461; 514/468; 514/486; 514/548; 514/549; 514/616; 514/618; 514/108; 514/119; 514/471; 514/472; 514/506
[58] Field of Search ..................................... 514/108, 119, 514/114, 118, 231.2, 315, 357, 374, 376, 377, 397, 406, 415, 424, 427, 461, 468, 471, 472, 506, 546; 547/486, 548, 549, 608, 550; 551/616, 618

[56] References Cited

U.S. PATENT DOCUMENTS

| | | | |
|---|---|---|---|
| 5,331,007 | 7/1994 | Griffith et al. ........................... | 514/522 |
| 5,378,729 | 1/1995 | Kohn et al. ........................... | 514/231.2 |
| 5,654,301 | 8/1997 | Kohn et al. ........................... | 514/231.2 |

OTHER PUBLICATIONS

Bardel, P., et al., "Synthesis and Anticonvulsant Activities of α–Acetamido–N–benzylacetamide Derivatives Containing an Electron–Deficient α–Heteroaromatic Substituent", *Journal of Medicinal Chemistry*, vol. 37, pp.4567–4571, (1994).

Choi, D., et al., "Synthesis and Anticonvulsant Activities of N–Benzyl–2–acetamidopropionamide Derivites", *Journal of Medicinal Chemistry*, vol. 39, pp. 1907–1916, (1996).

Kohn, H., et al., Preparation and Anticonvulsant Activity of a Series of Functionalized α–Aromatic and α–Heteroaromatic Amino Acids, *Journal of Medicinal Chemistry*, vol. 33, pp. 919–926, (1990).

*Primary Examiner*—Frederick Krass
*Attorney, Agent, or Firm*—Schwegman, Lundberg, Woessner & Kluth, P.A.

[57] ABSTRACT

The invention provides a therapeutic method for treating or preventing stroke and other ischemic disorders, as well as novel compounds and pharmaceutical compositions useful for carrying out such methods.

31 Claims, No Drawings

AMINO ACID DERIVATIVES USEFUL TO TREAT STROKE

PRIORITY OF INVENTION

This application claims priority under 35 U.S.C. §119(e) from U.S. Provisional Application No. 60/052,684, filed Jul. 15, 1997.

BACKGROUND OF THE INVENTION

Stroke or cerebrovascular disease is the name for several disorders that occur within seconds or minutes after the blood supply to the brain is disturbed. Symptoms may progress or fluctuate during the first day or two after onset; this is called evolution. When no further deterioration occurs, the condition is considered to be a completed stroke. The only warning signal that suggests susceptibility to a stroke is a transient ischemic attack (TIA). Strokes are characterized by the location and type of disturbance. The most common disturbance is a deficient supply of blood through an artery (ischemia). When this happens, the nerve tissue served by that artery rapidly loses its ability to function and may die. The dead tissue is called an infarct.

Stroke is the third leading cause of death in developed countries. Approximately 300,000 Americans suffer a stroke each year; one-fourth of them die, and half the survivors have long-term disabilities, including paralysis of face or extremities, speech disorders, loss of bladder function, inability to swallow or dementia. Stroke is more likely to occur in the elderly, and the risk doubles each decade after age 35 years. Five percent of the population older than 65 years has had a stroke.

Due to the lack of available pharmacotherapeutic agents, a significant percentage of the population subject to stroke or its after-effects are poorly managed. None of the drugs presently available are capable of preventing damage due to stroke and most, such as anticoagulants, have disturbing side effects. Clearly, current therapy has failed to "seize control" of this debilitating pathology. There is currently a need for pharmaceutical agents and methods that are useful for the treatment and prevention of stroke.

SUMMARY OF THE INVENTION

The invention provides a therapeutic method comprising treating a human afflicted with, or at risk of stroke, by administering an effective amount of a compound of formula (I):

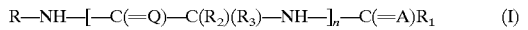

$$R\text{—}NH\text{—}[\text{—}C(=Q)\text{—}C(R_2)(R_3)\text{—}NH\text{—}]_n\text{—}C(=A)R_1 \quad (I)$$

wherein;

R is hydrogen, lower alkyl, lower alkenyl, lower alkynyl, aryl, aryl (lower alkyl), heterocyclic, heterocyclic (lower alkyl), (lower alkyl) heterocyclic, lower cycloalkyl, lower cycloalkyl (lower alkyl), and R is unsubstituted or is substituted with at least one electron withdrawing group, or electron donating group;

$R_1$ is hydrogen or lower alkyl, lower alkenyl, lower alkynyl, aryl (lower alkyl), aryl, heterocyclic, (lower alkyl) heterocyclic, heterocyclic (lower alkyl), lower cycloalkyl, lower cycloalkyl (lower alkyl), each unsubstituted or substituted with an electron donating group or an electron withdrawing group and $R_2$ and $R_3$ are independently hydrogen, lower alkyl, lower alkenyl, lower alkynyl, aryl (lower alkyl), aryl, heterocyclic, heterocyclic (lower alkyl), (lower alkyl) heterocyclic, lower cycloalkyl, lower cycloalkyl (lower alkyl), $SO_3^-$, or Z—Y wherein $R_2$ and $R_3$ may be unsubstituted or substituted with at least one electron withdrawing group or electron donating group;

Z is O, S, $S(O)_a$, $NR_4$, $PR_4$ or a chemical bond;

Y is hydrogen, lower alkyl, aryl, aryl (lower alkyl), lower alkenyl, lower alkynyl, halo, heterocyclic, heterocyclic (lower alkyl), (lower alkyl)heterocyclic, cycloalkyl, cycloalkyl (lower alkyl) and Y may be unsubstituted or substituted with an electron donating group or an electron withdrawing group, provided that when Y is halo, Z is a chemical bond;

or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$, $NR_4C(O)R_5$, $SC(O)R_5$, $NR_4CO_2R_5$, $SCO_2R_5$, $NR_4C(O)R_5R_6$, $NR_4C(O)NR_5S(O)_aR_6$, $NR_4C(S)R_5R_6$, $NR_4C(=Q)MNR_5C(=A)OR_6$, or $C(S)NH_2$;

$R_4$, $R_5$ and $R_6$ are independently hydrogen, lower alkyl, aryl, aryl (lower alkyl), lower alkenyl, or lower alkynyl, wherein $R_4$, $R_5$ and $R_6$ may be unsubstituted or substituted with an electron withdrawing group or an electron donating group;

$R_7$ is $R_6$, $COOR_8$, or $C(O)R_8$;

$R_8$ is hydrogen or lower alkyl, or aryl (lower alkyl), and the aryl or alkyl group may be unsubstituted or substituted with an electron withdrawing group or an electron donating group;

A and Q are independently O or S;

M is an alkylene chain containing up to 6 carbon atoms or a chemical bond;

n is 1–4; and a is 1–3;

or a pharmaceutically acceptable salt thereof.

The invention also provides novel compounds of formula (I) or pharmaceutically acceptable salts thereof that can be used to treat the effects of stroke, as well as novel processes and intermediates that are useful to prepare the novel compounds of formula (I).

The invention also provides novel pharmaceutical compositions comprising compounds of Formula (I) that are useful for the treatment of stroke.

The methods, compounds and compositions of the invention are useful for the treatment or prevention of stroke, including the effects of impaired cerebral blood, such as cerebral hemorrhage, thrombosis or embolism. The term treatment (or treat) includes the amelioration of at least one of the effects of the acute phase of stroke or its after-effects, such as those described hereinabove. It is believed that the compounds of formula (I) function, at least in part, by reduction of the brain damage caused by cerebral ischemia and its after-effects.

DETAILED DESCRIPTION OF THE INVENTION

The alkyl groups when used alone or in combination with other groups, are lower alkyl containing from 1 to 6 carbon atoms and may be straight chain or branched.

The aryl (lower alkyl) groups include, for example, benzyl, phenethyl, phenpropyl, phenisopropyl, phenbutyl, diphenylmethyl, 1,1-diphenylethyl, 1,2-diphenylethyl, and the like.

The term aryl, when used alone or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. The term polynuclear aromatics is meant to encompass bicyclic, tricyclic fused aromatic ring system containing from 10–18 ring carbon atoms and up to a total of 25 carbon atoms. The aryl group includes phenyl, and the polynuclear aromatics, e.g., naphthyl, anthracenyl, phenanthrenyl, azulenyl and the like. The aryl group also includes groups like ferrocenyl.

Lower alkenyl is an alkenyl group containing form 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E-)-4-methyl-2-pentenyl, pentadienyl, e.g., 1,3 or 2,4-pentadienyl, and the like.

The term cycloalkyl when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, norbornyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Furthermore, the substituents may either be in endo or exo positions in the bridged bicyclic systems.

The term "electron-withdrawing and electron donating" refer to the ability of a substituent to withdraw or donate electrons relative to that of hydrogen if the hydrogen atom occupied the same position in the molecule. These terms are well understood by one skilled in the art and are discussed in *Advanced Organic Chemistry*, by J. March, John Wiley and Sons, New York, N.Y., pp. 16–18 (1985), incorporated herein by reference. Electron withdrawing groups include halo, including bromo, fluoro, chloro, iodo and the like; nitro, carboxy, lower alkenyl, lower alkynyl, formyl, carboxyamido, aryl, quaternary ammonium, trifluoromethyl, aryl (lower alkanoyl), carbalkoxy and the like. Electron donating groups include such groups as hydroxy, lower alkoxy, including methoxy, ethoxy and the like; lower alkyl, such as methyl, ethyl, and the like; amino, lower alkylamino, di(lower alkyl) amino, aryloxy such as phenoxy, mercapto, lower alkylthio, lower alkylmercapto, disulfide (lower alkyldithio) and the like. One skilled in the art will appreciate that the aforesaid substituents may have electron donating or electron withdrawing properties under different chemical conditions. Moreover, the present invention contemplates any combination of substituents selected from the above-identified groups.

The term halo includes fluoro, chloro, bromo, iodo and the like.

The term acyl includes formyl and lower alkanoyl.

As employed herein, the heterocyclic substituent contains at least one sulfur, nitrogen or oxygen, but also may include more than one of N, S or non-peroxide O. The heterocyclic substituents contemplated by the present invention include heteroaromatics and saturated and partially saturated heterocyclic compounds. These heterocyclics may be monocyclic, bicyclic, tricyclic or polycyclic and include fused rings. They may contain up to 18 ring atoms, up to a total of 17 ring carbon atoms and a total of up to 25 carbon atoms. The heterocyclics are also intended to include the so-called benzoheterocycles. Representative heterocyclics include furyl, thienyl, pyrazolyl, pyrrolyl, imidazolyl, indolyl, thiazolyl, oxazolyl, isothiazolyl, isoxazolyl, piperidyl, pyrrolinyl, piperzinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolidinyl, imidazolinyl, imadazolidinyl, pyrrolidinyl, furazanyl, N-methylindolyl, methylfuryl, pyridazinyl, pyrmidinyl, pyrazinyl, pyridyl, 1,2-oxaethyl, aziridino, oxetanyl, azetidinyl, the N-oxides of the nitrogen containing heterocycles, such as the nitric oxides of pyridyl, pyrazinyl, and pyrimidinyl and the like. The preferred heterocyclic are thienyl, furyl, pyrrolyl, benzofuryl, benzothienyl, indolyl, methylpyrrolyl, morpholinyl, pyridyl, tetrahydrofuranyl, pyrazinyl, imidazolyl, pyrimidinyl, or pyridazinyl. The preferred heterocyclic is a 5- or 6-membered heterocyclic compound. The especially preferred heterocyclic is furyl, pyridyl, pyrazinyl, imidazolyl, pyrimidinyl, or pyridazinyl. The most preferred heterocyclic is furyl and pyridyl.

The preferred compounds are those wherein n is 1, but di, tri and tetrapeptides are also contemplated to be within the scope of the claims.

The preferred values of R is aryl (lower alkyl), especially benzyl, and the preferred $R_1$ is H or lower alkyl. The most preferred R, group is methyl.

The most preferred electron donating substituents and electron withdrawing substituents are halo, nitro, alkanoyl, formyl, arylalkanoyl, aryloyl, carboxyl, carbalkoxy, carboxamide, cyano, sulfonyl, sulfoxide, heterocyclic, guanidine, quaternary ammonium, lower alkenyl, lower alkynyl, sulfonium salts, hydroxy, allyloxy, lower alkoxy, preferably methoxy or ethoxy, lower (alkyl), amino, (lower alkyl)amino, di(lower alkyl-)amino, (amino lower alkyl) mercapto, mercaptoalkyl, alkylthio; and alkyldithio. The term "sulfide" encompasses mercapto, mercapto alkyl and alkylthio, while the term disulfide encompasses alkyldithio. These preferred substituents may be substituted on any one of $R_1$, $R_2$, $R_3$, $R_4$, $R_5$ or $R_6$, $R_7$ or $R_8$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenyoxy; amino; alkyl-amino, such as methylamino, ethylamino; arylamino, such as anilino; lower dialkylamino, such as, dimethylamino; trialkyl ammonium salt, hydrazino, alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein R$_{18}$ is lower alkyl], N-lower alkylhydroxyl amino [(NR$_{18}$)OH wherein R$_{18}$ is lower alkyl], N-lower alkyl-O-lower alkyl hydroxyamino, i.e., [N(R$_{18}$)OR$_{19}$ wherein R$_{18}$ and R$_{19}$ are independently lower alkyl] and o-hydroxylamino (—O—NH$_2$); alkylamido such as acetamido, trifluoroacetamido, lower alkoxyamino, (e.g. NH(OCH$_3$); and (heterocyclic) amino, such as pyrazoylamino.

The heterocyclic groups representative of $R_2$ and $R_3$ have the formula XI as disclosed in U.S. Pat. No. 5,378,729, which is incorporated by reference herein.

It is preferred that one of $R_2$ and $R_3$ is hydrogen.

In a preferred embodiment, one of $R_2$ and $R_3$ is hydrogen and that the other is (lower alkoxy)-lower alkyl or heterocyclic. It is preferred that one of $R_2$ and $R_3$ is methoxymethyl or is a heterocyclic having Formula XI. The preferred heterocyclics include furyl, thienyl, benzothienyl, benzofuryl, oxazolyl, thiazolyl, isoxazolyl, indolyl, pyrazolyl, isoxazolidinyl, benzothienyl, benzofuryl, morpholinyl, indolyl, pyrolyl, furfuryl, and methylpyrrolyl, pyridyl, pyrazinyl, imidazolyl, pyrimidinyl or pyridazinyl. In another preferred embodiment, one of $R_2$ and $R_3$ is alkyl (e.g., methylisopropyl), aryl (e.g., phenyl), 2-thiomethylethyl, lower alkoxy (e.g., ethoxy, methoxy), anilino, propenyl, alkyl-amino (e.g., ethylamino or methylamino). In another preferred embodiment, one of $R_2$ and $R_3$ is hydrogen and the other is heterocyclic lower alkyl, lower alkenyl, amino, lower alkoxy amino, N-lower alkylhydroxyamino, lower alkoxyamino, N-lower alkyl-O-lower alkylhydroxyamino or aralkoxycarbonylhydrazino.

A preferred compound that is useful to treat stroke is a compound of formula:

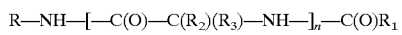

wherein;

R is hydrogen, lower alkyl, lower alkenyl, lower alkynyl, aryl, aryl (lower alkyl), heterocyclic, heterocyclic (lower alkyl), (lower alkyl) heterocyclic, lower cycloalkyl, lower cycloalkyl (lower alkyl), and R is unsubstituted or is substituted with at least one electron withdrawing group, or electron donating group;

$R_1$ is hydrogen or lower alkyl, lower alkenyl, lower alkynyl, aryl (lower alkyl), aryl, heterocyclic, (lower alkyl) heterocyclic, heterocyclic (lower alkyl), lower cycloalkyl, lower cycloalkyl (lower alkyl), each unsubstituted or substituted with an electron donating group or an electron withdrawing group and $R_2$ and $R_3$ are independently hydrogen, lower alkyl, lower alkenyl, lower alkynyl, aryl (lower alkyl), aryl, heterocyclic, heterocyclic (lower alkyl), (lower alkyl) heterocyclic, lower cycloalkyl, lower cycloalkyl (lower alkyl), or Z—Y wherein $R_2$ and $R_3$ may be unsubstituted or substituted with at least one electron withdrawing group or electron donating group;

Z is O, S, $S(O)_\alpha$, $NR_4$, $PR_4$ or a chemical bond;

Y is hydrogen, lower alkyl, aryl, aryl (lower alkyl), lower alkenyl, lower alkynyl, halo, heterocyclic, heterocyclic (lower alkyl), (lower alkyl)heterocyclic and Y may be unsubstituted or substituted with an electron donating group or an electron withdrawing group, provided that when Y is halo, Z is a chemical bond;

or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$, $NR_4C(O)R_5$, $SC(O)R_5$, $NR_4CO_2R_5$, $SCO_2R_5$;

$R_4$, $R_5$ and $R_6$ are independently hydrogen, lower alkyl, aryl, aryl (lower alkyl), lower alkenyl, or lower alkynyl, wherein $R_4$, $R_5$ and $R_6$ may be unsubstituted or substituted with an electron withdrawing group or an electron donating group;

$R_7$ is $R_6$, $COOR_8$, or $C(O)R_8$;

$R_8$ is hydrogen or lower alkyl, or aryl (lower alkyl), and the aryl or alkyl group may be unsubstituted or substituted with an electron withdrawing group or an electron donating group;

n is 1–4; and a is 1–3;

or a pharmaceutically acceptable salt thereof.

A preferred compound that is useful to treat stroke is a compound of formula:

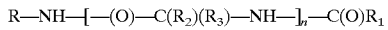

wherein $R_1$ is H or lower alkyl, $R_2$ and $R_3$ are as defined above and A is hydrogen or an electron donating group or electron-withdrawing group and m is 0–5. It is preferred that A is hydrogen (i.e., m=0). However, values of m equaling 1, 2 or 3 are also preferred.

A preferred compound that is useful to treat stroke is a compound of formula:

R—NH—[—(O)—C($R_2$)($R_3$)—NH—]$_n$—C(O)$R_1$ wherein R and $R_1$, independently, are hydrogen, lower alkyl, lower alkenyl, lower alkynyl, aryl (lower alkyl), aryl, heterocyclic, or (lower alkyl) heterocyclic, each unsubstituted or substituted with at least one substituent;

$R_2$ and $R_3$, independently, are hydrogen, lower alkyl, lower alkenyl, lower alkyl heterocyclic, each unsubstituted or substituted with at least one substituent, preferably lower alkoxy; halogen or a heteroatom containing oxygen, nitrogen, sulfur or phosphorous substituted with hydrogen, lower alkyl or aryl, said lower alkyl or aryl groups being substituted or unsubstituted; and n is 1 to 4.

Another preferred compound that is useful to treat stroke is a compound of formula:

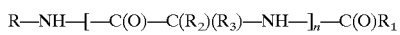

wherein R is aryl, aryl (lower alkyl), heterocyclic, (lower alkyl) heterocyclic, polynuclear aromatic or (lower alkyl) polynuclear aromatic, each unsubstituted or substituted with at least one electron withdrawing substituent or at least one electron donating substituent;

$R_1$ is H or lower alkyl, such as methyl, unsubstituted or substituted with at least one electron withdrawing substituent or at least one electron donating substituent;

$R_2$ and $R_3$, independently, are hydrogen, lower alkyl, lower alkenyl, lower alkynyl, aryl, aryl (lower alkyl), heterocyclic, (lower alkyl) heterocyclic, polynuclear aromatic, (lower alkyl) polynuclear aromatic, each unsubstituted or substituted with at least one electron donating substituent, such as alkoxy; halogen or a heteroatom containing oxygen, nitrogen, sulfur or phosphorous substituted with hydrogen, lower alkyl or aryl, said lower alkyl or aryl groups being substituted or unsubstituted; and n is 1 to 4.

Another preferred compound that is useful to treat stroke is a compound of formula:

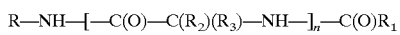

wherein R is aryl (lower alkyl), heterocyclic, (lower alkyl) heterocyclic, polynuclear aromatic or (lower alkyl) polynuclear aromatic, each of which may be unsubstituted or substituted with at least one halo, nitro, acyl, carboxyl, carboalkoxy, carboxamide, cyano, sulfonyl, sulfoxide (sulfinyl), heterocyclic, guanidine, quaternary ammonium hydroxy, alkoxy, alkyl, amino, phenoxy, mercapto, sulfide or disulfide;

$R_1$ is H or lower alkyl which may be unsubstituted or substituted with at least one halo, nitro, acyl, carboxamide, cyano, sulfonyl, sulfoxide (sulfinyl), heterocyclic, guanidine, quaternary ammonium, hydroxy, lower alkoxy, amino, phenoxy, sulfide, or disulfide;

$R_2$ is hydrogen, lower alkyl, lower alkenyl, lower alkynyl, aryl, heterocyclic, (lower alkyl) heterocyclic, polynuclear aromatic, (lower alkyl) polynuclear aromatic, each unsubstituted or substituted with at least one electron withdrawing substituent or at least one electron donating substituent; halogen or a heteroatom consisting of oxygen, nitrogen, sulfur or phosphorous, said heteroatom being substituted with hydrogen, lower alkyl or aryl, said lower alkyl or aryl groups being substituted or unsubstituted;

$R_3$ is hydrogen, lower alkyl, lower alkenyl, lower alkynyl, aryl, heterocyclic, (lower alkyl) heterocyclic, polynuclear aromatic, (lower alkyl) polynuclear aromatic, each unsubstituted or substituted with at least one electron withdrawing substituent or at least one electron donating substituent, such as alkoxy; halogen or a heteroatom consisting of oxygen, nitrogen, sulfur, or phosphorous, said heteroatom being substituted with hydrogen, lower alkyl or aryl, said lower alkyl or aryl groups being substituted or unsubstituted;

and n is 1 to 4;

Another preferred compound that is useful to treat stroke is a compound of formula:

wherein R is aryl, aryl (lower alkyl), heterocyclic or heterocyclic (lower alkyl) and R is unsubstituted or is substituted with at least one electron withdrawing group, or electron donating group;

$R_1$ is hydrogen or lower alkyl, unsubstituted or substituted with an electron donating group or an electron withdrawing group and $R_2$ and $R_3$ are independently hydrogen, lower alkyl, lower alkenyl, lower alkynyl, aryl (lower alkyl), aryl, heterocyclic, heterocyclic (lower alkyl), or Z—Y wherein $R_2$ and $R_3$ may be unsubstituted or substituted with at least one electron withdrawing group or electron donating group;

Z is O, S, $S(O)_\alpha$, $NR_4$, $PR_4$ or a chemical bond;

Y is hydrogen, lower alkyl, aryl, aryl (lower alkyl), lower alkenyl, lower alkynyl, heterocyclic, heterocyclic (lower alkyl), or halo and Y may be unsubstituted or substituted with an electron donating group or an electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4R_5R_7$.

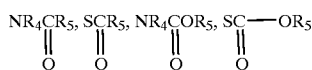

$R_4$, $R_5$ and $R_6$ are independently hydrogen, lower alkyl, aryl, aryl (lower alkyl), lower alkenyl, or lower alkynyl, wherein $R_4$, $R_5$ and $R_6$ may be unsubstituted or substituted with an electron withdrawing group or an electron donating group, and $R_7$ is $R_6$ or $COOR_8$ or $COR_8$, $R_8$ is hydrogen or lower alkyl, or aryl (lower alkyl), wherein the aryl or lower alkyl groups may be unsubstituted or substituted with an electron withdrawing or electron donating group, n is 1–4 and a is 1–3.

Another preferred compound that is useful to treat stroke is a compound of formula:

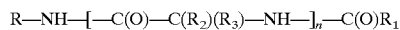

wherein R is aryl, aryl lower alkyl, heterocyclic or heterocyclic alkyl which is unsubstituted or substituted with at least one electron withdrawing group or at least one electron donating group;

$R_1$ is hydrogen or lower alkyl which is unsubstituted or substituted with at least one electron withdrawing group or one electron donating group, $R_2$ and $R_3$ are independently hydrogen, lower alkenyl, lower alkynyl, aryl, aryl (lower alkyl), Z—Y, or a heterocyclic group which may be unsubstituted or substituted with at least one electron withdrawing or one electron donating group, with the proviso that $R_2$ and $R_3$ cannot both by hydrogen;

Z is O, S, $NR_4$, $PR_4$ or a chemical bond;

Y is hydrogen, lower alkyl, aryl, aryl (lower alkyl), lower alkenyl, lower alkynyl or halo, and Y may be unsubstituted or substituted with an electron donating group or an electron withdrawing group, provided that when Y is halo, Z is a chemical bond; or ZY taken together is $NR_4NR_5R_6$, $NR_4OR_5$, $ONR_4R_5$, $OPR_4R_5$, $PR_4OR_5$, $SNR_4R_5$, $NR_4SR_5$, $SPR_4R_5$, $PR_4SR_5$, $NR_4PR_5R_6$, $PR_4NR_5R_6$, $R_4$, $R_5$ and $R_6$ are independently hydrogen, lower alkyl, aryl, aryl (lower alkyl), lower alkenyl, or lower alkynyl, wherein $R_4$, $R_5$ and $R_6$ may be unsubstituted or substituted with an electron withdrawing group or an electron donating group;

n is 1–4.

It is especially preferred that n is 1.

Another preferred compound that is useful to treat stroke is a compound wherein R is aryl, aryl (lower alkyl), such as benzyl; heterocyclic, or heterocyclic (lower alkyl), $R_1$ is hydrogen or lower alkyl, such as methyl; $R_2$ and $R_3$ are independently hydrogen, heterocyclic, lower alkyl, aryl, lower alkoxy, lower alkoxy (lower alkyl), lower alkenyl, amino, hydroxylamino, lower alkoxy amino, N-lower alkyl hydroxy-amino, N-lower alkyl-O-lower alkyl hydroxyamino, aralkoxy carbonyl hydrazino or alkylmercapto, and n is 1.

Another preferred compound that is useful to treat stroke is a compound wherein n is 1, R and $R_1$ are as defined hereinabove and one of $R_2$ and $R_3$ is hydrogen and the other is heterocyclic, heterocyclic (lower alkyl), aryl N-hydroxyamino, lower alkoxyamino, N-lower alkylhydroxylamino, N-lower alkyl-O-lower alkylhydroxyamino.

Another preferred compound that is useful to treat stroke is a compound wherein n is 1, R and $R_1$ are as defined hereinabove, one of $R_2$ and $R_3$ is as defined hereinabove or the other is heterocyclic, heterocyclic (lower alkyl), (lower alkyl) heterocyclic, aryl, N-hydroxylamino, lower alkoxy amino, N-lower alkyl hydroxylamino, N-lower alkyl-O-lower alkyl hydroxylamino, lower alkoxy, dialkyl lower amino, lower alkylamino, aryl lower alkylcarbonyl hydrazino, or lower alkylmercapto.

Another preferred compound that is useful to treat stroke is a compound wherein $R_2$ is hydrogen; and $R_3$ is 2-furyl, 2-pyrrolyl, 1-pyrazolyl, 2-oxazolyl, 2-thiazolyl, pyridyl, pyrazinyl, or pyrimidinyl.

Another preferred compound that is useful to treat stroke is a compound wherein $R_2$ is hydrogen; $R_3$ is $NR_4OR_5$; $R_4$ is hydrogen or lower alkyl; and $R_5$ is lower alkyl.

Another preferred compound that is useful to treat stroke is a compound wherein R is benzyl, substituted with at least one electron withdrawing substituent or at least one electron donating substituent.

The various combination and permutations of the Markush groups of $R_1$, $R_2$, $R_3$ R and n described herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$ and R with respect to each value of n.

The compounds of the present invention may contain one (1) or more asymmetric carbons and may exist in racemic and optically active forms. The configuration around each asymmetric carbon can be in either the D or L form. (It is well known in the art that the configuration around a chiral carbon atoms can also be described as R or S in the Cahn-Prelog-Ingold nomenclature system). All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atoms to which the groups $R_2$ and $R_3$ are attached as substituted. When n is 1, the compounds of the present invention is of the formula:

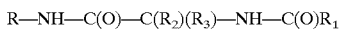

wherein R, $R_1$, $R_2$, $R_3$, $R_4$, $R_5$, $R_6$, Z and Y are as defined previously, and C(O) represents a carbonyl group. As used herein, the term configuration shall refer to the configuration around the carbon atom to which $R_2$ and $R_3$ are attached, even though other chiral centers may be present in the molecule. Therefore, when referring to a particular configuration, such as D or L, it is to be understood to mean the stereoisomer, including all possible enantiomers and diastereomers. The compounds of the present invention are directed to all of the optical isomers, i.e., the compounds of the present invention are either the L stereoisomer or the D-stereoisomer. These stereoisomers may be found in mixtures of the L and D stereoisomer, e.g., racemic mixtures. The D stereoisomer or R configuration is preferred.

The present compounds can be prepared in accord with Scheme I-VI and the working examples of U.S. Pat. No. 5,378,729, and as disclosed by D. Choi et al., *J. Med. Chem.*, 39, 1907 (1996), P. Bardel et al., *J. Med. Chem.*, 37, 4567 (1994) and H. Kohn et al., *J. Med. Chem.*, 33, 919 (1990), which are incorporated by reference herein.

The compounds can also be prepared using procedures described in U.S. Pat. No. 5,654,301, which is incorporated by reference herein. In particular, these procedures can be used to prepare compounds wherein Q or A is thioxo (=S).

Resulting mixtures of isomers can be separated in the pure isomers by methods known to one skilled in the art, e.g., by fractional distillation, crystallization and/or chromatography. Optically pure functionalized amino acid derivatives can be prepared directly from the corresponding pure chiral intermediate, such as an optically active amino acid. Racemic products can likewise be resolved into the optical antipodes, for example, by separation of diastereomeric salts thereof, e.g., by fractional crystallization, by selective enzymatic hydrolysis, e.g., papain digestion, or by use of a chiral stationary phase in chromatography (HPLC). For a discussion of chiral stationary phases for HPLC, See, DeCamp, Chirality, 1, 2–6 (1989), which is incorporated herein by reference with the same force and effect as if fully set forth herein.

For example, a racemic mixture of any of the intermediate in any of the schemes, wherein $R_1$ is H is reacted with an optically active amine, $RNH_2$, e.g., (R)(+)α-methyl-benzylamine to form a pair of diastereomeric salts. Diastereomers can then be separated by recognized techniques known in the art, such as fractional recrystallization and the like.

In another method, a racemic mixture of final products or intermediates can be resolved by using enzymatic methods. Since enzymes are chiral molecules, an optically pure enzyme can be used to separate the racemic mixture, since it will preferentially act on one of the compounds, without affecting the enantiomer. For example, acylase, such as acylase I, can be used to separate the racemic modification of an intermediate D,L(±)α-acetamido-2-furanacetic acid. It acts on the L(±)α-acetamido-2-furanacetic acid, but will not act on the D enantiomer. In this way, the D(−)α-acetamido-2-furanacetic acid can be isolated. The intermediate can then react with the amine ($RNH_2$) under amide forming conditions as described hereinabove to form the compound of Formula (I).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula (I) can be formulated as pharmaceutical compositions and administered to a mammalian host, such as a human patient in a variety of unit dosage or sustained release forms adapted to the chosen route of administration, i.e., orally or parenterally, by intravenous, intrathecal, intramuscular, topical or subcutaneous routes.

Thus, the present compounds may be systemically administered, e.g., orally, in combination with a pharmaceutically acceptable vehicle or carrier such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices, such as patches or implantable depots or pumps.

The active compound may also be administered intravenously, intrathecally, intraperitoneally, or by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection, inhalation, insufflation or infusion can include sterile aqueous solutions or dispersions or sterile powders comprising the active ingredient which are adapted for the extemporaneous preparation of sterile injectable or infusible solutions or dispersions, optionally encapsulated in liposomes or biodegradable polymeric microparticles. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable or infusable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 5 to about 1000 mg, with from about 250 to about 750 mg being preferred. Expressed in proportions, the active compound is generally present in from about 10 to about 750 mg/ml of carrier. In the case of compositions containing supplementary active ingredients, the dosages are determined by reference to the usual dose and manner of administration of the said ingredients.

The active ingredients of the therapeutic compositions and the compounds of the present invention can exhibit anti-stroke activity when administered in amounts ranging from about 1 mg to about 100 mg per kilogram of body weight per day. A preferred dosage regimen for optimum results would be from about 10 mg to about 50 mg per kilogram of body weight per day, and such dosage units are employed that a total of from about 0.5 gram to about 3.0 grams of the active compound for a subject of about 70 kg of body weight are administered in a 24-hour period. This dosage regimen may be adjusted to provide the optimum therapeutic response and is preferably administered one to three times a day in dosages of about 600 mg per administration. For example, several divided doses may be administered daily or the dose may be proportionally reduced as indicated by the exigencies of the therapeutic situation. A decided practical advantage is that the active compound may be administered in a convenient manner such as by the oral, intravenous (where water soluble), intramuscular or subcutaneous routes.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The invention will be further described by reference to the following detailed examples, wherein full spectral data are available in D. Choi et al., *J. Med. Chem.*, 39, 1907 (1996).

EXAMPLE 1

Synthesis of (S)-enriched N-Benzyl-2-aminohydracrylamide ((S)-7)

To a stirred methanolic solution (250 mL) of L-serine methyl ester hydrochloride ((S)-6) (20.00 g, 128 mmol) was added benzylamine (55.9 mL, 512 mmol), and then the reaction solution was heated at reflux (18 h). The solvent was removed under reduced pressure, the insoluble salts were filtered, and the excess benzylamine was removed under high vacuum (Kugelrohr). The residue was dissolved in $H_2O$ (100 mL), and the product was extracted with $CHCl_3$ (8×200 mL). The organic layers were combined and dried ($Na_2SO_4$), and the solvent was removed under reduced pressure. The residue was triturated with $Et_2O$ (150 mL) and filtered to give 8.50 g (34%) of the product as a white solid: mp 76–80° C.

EXAMPLE 2

Synthesis of (R)-enriched N-Benzyl-2-aminohydracrylamide ((R)-7)

HCl (8.00 g, 219.4 mmol) was passed into MeOH (250 mL), and then D-serine ((R)-5) (20.00 g, 190.3 mmol) was added. The reaction solution was heated at reflux (18 h), then benzylamine (81.6 mL, 761 mmol) was added, and then the reaction mixture was heated for additional 18 h. The solvent was removed under reduced pressure, the insoluble salts were filtered, and the excess benzylamine was removed under high vacuum (Kugelrohr). The residue was dissolved in H$_2$O (100 mL), and the product was extracted with CHCl$_3$ (8×200 mL). The organic layers were combined and dried (Na$_2$SO$_4$), and the solvent was removed under reduced pressure. The residue was triturated with Et$_2$O (150 mL) and filtered to vie 10.0 g (27%) of the product as white solid: mp 74–78° C.; $[\alpha]^{23}_D$ (c=1, MeOH)=1.6°.

EXAMPLE 3

Synthesis of (S)-N-Benzyl-2-acetamidohydracrylamide ((S)-9)

To a stirred CH$_2$Cl$_2$ suspension (100 mL) of enriched (S)-7 (8.50 g, 43.7 mmol) was added Ac$_2$O (5.0 mL, 52.4 mmol), and then the reaction suspension was stirred at room temperature (1 h). The solvent was removed under reduced pressure to give a white solid. The product was triturated with Et$_2$O (250 mL) to give 8.50 g (82%) of enriched (S)-27 as a white solid. The reaction product was recrystallized (3×) using EtOH to give 1.89 g (18%) of (S)-27: mp 147–148° C.

EXAMPLE 4

Synthesis of (R)-N-Benzyl-2-acetamidohydracrylamide ((R)-9)

Using the preceding procedure and enriched (R)-7 (10.00 g, 51.5 mmol) and Ac$_2$O (5.8 mL, 61.8 mmol) gave 7.60 g (62%) of enriched (R)-9 as a white solid. The reaction product was recrystallized (2×) using EtOH to give 3.50 g (29%) of (R)-27: mp 148–149° C.; $[\alpha]^{23}_D$ (c=1, MeOH)=+22.4°.

EXAMPLE 5

Synthesis of (S)-N-Benzyl-2-acetamido-3-methoxypropionamide ((S)-1)

To a stirred Ch$_3$CN solution (300 mL) of (S)-9 (1.65 g, 7 mmol) were successively added Ag$_2$O (8.11 g, 35 mmol) and MeI (4.4 mL, 70 mmol) at room temperature. the reaction mixture was stirred at room temperature (4 d). The insoluble salts were filtered, and the solvents were removed n vacuo to give a white solid. The residue was triturated with Et$_2$O (100 mL) to give 1.40 g (80%) of (S)-1.

EXAMPLE 6

Synthesis of (R)-N-Benzyl-2-acetamido-3-methoxypropionamide ((R)-1)

Using the preceding procedure and (R)-9 (2.36 g, 10 mmol), Ag$_2$O (11.59 g, 50 mmol), and MeI (6.2 mL, 100 mmol) gave 2.20 g (88%) of (R)-1 after stirring at room temperature (4 d): mp 143–144° C.; $[\alpha]^{23}_D$ (c=1, MeOH)=+16.4°.

EXAMPLE 7

Pharmacological Studies

Studies were conducted to examine the possible therapeutic efficacy of compound (R)-1 in an animal model of induced focal brain ischemia (see A. Tamura et al., *J. Cerebral Blood Flow and Metab.*, 1, 53 (1981); X. Cao et al., *Brain Res.*, 644, 267 (1994)). The ischemic insult was effected by permanent unilateral occlusion of a middle cerebral artery in rats. This model is one of many that have been developed to mimic human stroke sequela and brain damage, and to evaluate the efficacy of potential therapies for the treatment of human stroke.

1. Drugs and Chemicals

Chloral hydrate (Sigma, St. Louis, Mo. 63178 USA), MK-801 (RBI, Natick MA 01760-2447 USA), Kanamycin (Sigma, St. Louis, Mo. 63178 USA), 10% Povidone iodine solution (T. K., Taiwan), Pyrogen free saline (Astar, Taiwan) and 2% Crystal Violet (Delta, Taiwan) were used.

2. Equipment

Dental drill (UPOWER UG 33, SELECTOR-M), Image Analyzer (Life Science Resources VISTA Version 3.0), Infant Incubator (Brighten Life BL-90-SC), Magnifying stereomicroscope (ZEISS, Stemi 1000), Microscissors (A. Heiss), Microtome (SHANDON, Varistain 24-4 Automatic Slide), Microinjection Pump (Syringe Driver-Type MS 16A Graseby Medical) and Rectal thermistor probe (Harvard Hemeothermic Blanket Control Unit) were used.

3. Animals

Male Wistar rats weighing 150–200 gms (10 weeks of age) from the Animal Resources Center, medical College of National Taiwan University were used. The animals were housed separately in positive pressure stainless steel isolation racks (NuAire®, Mode: NU-605, airflow velocity 50±5 ft/min, HEPA Filter). APEC® cages contained 6 rats (in cm, 45 length×23 width×15 height). The animals were maintained in a controlled temperature (22°–24° C.) and humidity (60%–80%) environment with 12 hour light dark cycles for at least one week in the laboratory prior to use. Free access to standard lab chow (Fwusow Industry Limited Co.) and tap water was granted. All aspects of this work, i.e., housing, experimentation and disposal of animals were performed in general accordance with the International Guiding Principles for Biomedical Research Involving Animals (CIOMS Publication No. ISBN 92 90360194, 1985).

4. Methods

The permanent brain ischemia via middle cerebral artery occlusion (MCAO) was carried out under general anesthesia induced by chloral hydrate (500 mg/10 ml/kg i.p.). The temporoparietal region was shaved and a skin incision was made between the lateral aspect of the orbit and the external acoustic meatus. The superior pole of the parotid gland was reflected downwards as was the temporalis muscle after partial resection of its cranial insertion. The distal course of the middle cerebral artery was then visible through the translucent skull.

Under a 10× magnifying stereomicroscope (ZEISS, Stemi 1000), a craniectomy was performed with a dental drill and then enlarged with fine synovectomy rongeurs. The exposed middle cerebral artery was cut with microscissors and the temporalis and parotid gland were replaced. The incision area was lightly dusted with kanamycin (Sigma, St. Louis, Mo. 63178 USA), the scalp was sutured and a 10% povidone iodine solution (T. K., Taiwan) was topically applied. During surgery, the animals were maintained normothermic (37.5±1.0° C.) by means of a homeothermic heating system coupled to a rectal thermistor probe (Harvard Homeothermic Blanket Control Unit). Following surgery, the animals were kept normothermic in an Infant Incubator (Brighten Life BL-90-SC) for about 1 hour while recovering from anesthesia. After recovery, the rats were housed 5 per cage with free access to food and water and kept in a clean animal room.

The test compound (R)-1 was administered to rats 15 minutes before occlusion at a dose of 25 mg/kg IP followed by 5 mg/kg/hour IV infusion for 4 hours. The reference agent MK-801 was also administered 15 minutes before occlusion at a dose of 0.5 mg/kg IP followed by 0.5 mg/kg/4 hours IV infusion. Vehicle (PBS, pH 7.4) was similarly administered at a volume of 5 ml/kg IP 15 minutes before occlusion followed by 5 ml/kg/4 hour IV infusion. Body temperature was recorded at pretreatment of test substances and at 30 minutes after IP injection as well as 30 minutes after IV (4 hours) perfusion.

On the fourth day after the ischemic insult, the animals were sacrificed by decapitation. Their brains were rapidly removed and frozen at −70° C. in a deep freezer. Twenty-four house later, whole brain coronal sections (20 $\mu$m) were sliced by microtome ("SHANDON" Varistain 24-4 Automatic Slide). Every 20th section (i.e., 400 $\mu$m apart) was selected for histological examination. Altogether thirty slices, stained by 2% crystal violet, were used to measure the area of ischemia damage. This was quantitatively assessed by an Image Analyzer (Life Science Resources VISTA Version 3.0). The total ischemic area (mm$^2$) of each coronal slice from each animal was accumulated and expressed as the mean±S.E.M. The calculated infarcted volume (mm$^2$ in total distance of 12 mm) of focal cerebral ischemia was expressed as the mean±S.E.M. for each experimental group. The percent protection obtained for each test substance treated group compared to the vehicle treated group was also calculated.

5. Results

Under these experimental conditions, MCAO caused a reproducible ischemia of about 20%–25% of the affected hemisphere. For the most part, the area of damage was largely continued to various cortical regions (i.e., frontal, sensorimotor, auditory and occipital cortices) and only rarely involved damage to components of the basal ganglia. The area of infarct was quantitatively assessed in 30 anterior to posterior coronal slices for each animal. Compound (R)-1 (total dose of 1 mg/kg) reduced the total infarct volume by 75.3±7.1%; however, 1 out of 5 tested animals were dead within 72 hours after MK-801 treatment. Compound (R)-1 (total dose of 45 mg/kg) significantly reduced the total infarct volume by 72.8±6.8% (n=5); no mortality was seen in these animals. These results are summarized on Table 1, below.

TABLE 1

Effect of (R)-1 and MK-801 relative to Vehicle on the
Total Volume of Ischemic Lesions in the Brains of MCAO Rats

| Compound | Route | Dose | N | Infarcted (X ± SEM mm$^2$) | % Inh. (X ± SEM) |
|---|---|---|---|---|---|
| Vehicle (PBS) | IP/IV | 5 ml/kg | 5 | 83.52 ± 11.29 | — |
| MK-801 | IP/IV | *1 mg/kg | 5 | 20.61 ± 5.83 | 75.3 ± 7.11 |
| (R)-1 | IP/IV | 45 mg/kg | 5 | 22.49 ± 5.71 | 72.8 ± 6.8 |

*1 out of 5 animals were dead 71 hours after MK-801 treatment at dose of 0.5 mg/kg, i.p. and 0.5 mg/kg/4 hours i.v. infusion.

These studies confirm the neuroprotective effect previously observed for MK-801 in this rat model of brain focal ischemia induced by permanent, unilateral middle cerebral artery occlusion. The test compound, (R)-1, revealed a similar and significant neuroprotective effect in this model. No significant changes in body temperature were seen during or at 30 minutes after compound administration.

All patents, patent documents and publications cited hereinabove are incorporated by reference herein. While the invention has been described with reference to certain preferred embodiments, those skilled in the art will realize that changed and modifications may be made thereto without departing from the full and intended scope of the appended claims.

What is claimed is:

1. A therapeutic method comprising treating a human afflicted with, or at risk of stroke, by administering thereto an effective amount of a compound of formula (I):

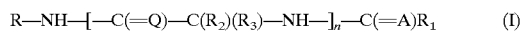

$$R-NH-[-C(=Q)-C(R_2)(R_3)-NH-]_n-C(=A)R_1 \qquad (I)$$

wherein;

R is hydrogen, lower alkyl, lower alkenyl, lower alkynyl, aryl, aryl (lower alkyl), heterocyclic, heterocyclic (lower alkyl), (lower alkyl) heterocyclic, lower cycloalkyl, or lower cycloalkyl (lower alkyl), and R is unsubstituted or is substituted with at least one electron withdrawing group, or electron donating group;

$R_1$ is hydrogen, lower alkyl, lower alkenyl, lower alkynyl, aryl (lower alkyl), aryl, heterocyclic, (lower alkyl) heterocyclic, heterocyclic (lower alkyl), lower cycloalkyl, or lower cycloalkyl (lower alkyl), each unsubstituted or substituted with an electron donating group or an electron withdrawing group and $R_2$ and $R_3$ are independently hydrogen, lower alkyl, lower alkenyl, lower alkynyl, aryl (lower alkyl), aryl, heterocyclic, heterocyclic (lower alkyl), (lower alkyl) heterocyclic, lower cycloalkyl, lower cycloalkyl (lower alkyl), $SO_3^-$, or Z—Y wherein $R_2$ and $R_3$ may be unsubstituted or substituted with at least one electron withdrawing group or electron donating group;

Z is O, S, S(O)$_a$, $NR_4$, $PR_4$ or a chemical bond;

Y is hydrogen, lower alkyl, aryl, aryl (lower alkyl), lower alkenyl, lower alkynyl, halo, heterocyclic, heterocyclic (lower alkyl), (lower alkyl)heterocyclic; cycloalkyl or cycloalkyl (lower alkyl) and Y may be unsubstituted or substituted with an electron donating group or an electron withdrawing group, provided that when Y is halo, Z is a chemical bond;

or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$, $NR_4C(O)R_5$, $SC(O)R_5$, $NR_4CO_2R_5$, $SCO_2R_5$, $NR_4C(O)R_5R_6$, $NR_4C(O)NR_5S(O)_aR_6$, $NR_4C(S)R_5R_6$, $NR_4C(=Q)MNR_5C(=A)OR_6$, or $C(S)NH_2$;

$R_4$, $R_5$ and $R_6$ are independently hydrogen, lower alkyl, aryl, aryl (lower alkyl), lower alkenyl, or lower alkynyl, wherein $R_4$, $R_5$ and $R_6$ may be unsubstituted or substituted with an electron withdrawing group or an electron donating group;

$R_7$ is $R_6$, $COOR_8$, or $C(O)R_8$;

$R_8$ is hydrogen, lower alkyl, or aryl (lower alkyl), and the aryl or alkyl group may be unsubstituted or substituted with an electron withdrawing group or an electron donating group;

A and Q are independently O or S;

M is an alkylene chain containing up to 6 carbon atoms or a chemical bond;

n is 1–4; and a is 1–3;

or a pharmaceutically acceptable salt thereof.

2. A therapeutic method comprising treating a human afflicted with, or at risk of, stroke, by administering thereto an effective amount of a compound of the formula:

$$R-NH-[-C(O)-C(R_2)(R_3)-NH-]_n-C(O)R_1$$

wherein;

R is aryl, aryl (lower alkyl), heterocyclic (lower alkyl), lower alkyl, or heterocyclic, each unsubstituted or substituted with at least one electron withdrawing substituent or at least one electron donating substituent;

$R_1$ is H or lower alkyl, unsubstituted or substituted with at least one electron withdrawing substituent or at least one electron donating substituent;

$R_2$ and $R_3$, independently, are hydrogen, lower alkyl, lower alkenyl, lower alkynyl, aryl, aryl (lower alkyl), heterocyclic (lower alkyl), or heterocyclic, each unsubstituted or substituted with at least one electron withdrawing substituent or at least one electron donating substituent; or $R_2$ and $R_3$, independently, are halogen, nitrogen, oxygen or sulfur, each substituted with hydrogen, lower alkyl or aryl, said lower alkyl or aryl groups being substituted or unsubstituted; and n is 1 to 4;

or a pharmaceutically acceptable salt thereof.

3. The method of claim 1 wherein R is aryl (lower alkyl), heterocyclic (lower alkyl) or heterocyclic, each of which may be unsubstituted or substituted with at least one halo, nitro, acyl, carboxyl, carboalkoxy, carboxamide, cyano, sulfonyl, sulfoxide, heterocyclic, guanidine, quaternary ammonium, hydroxy, lower alkoxy, lower alkyl, amino, or phenoxy;

$R_1$ is H or lower alkyl which may be unsubstituted or substituted with at least one halo, nitro, acyl, carboxamido, cyano, sulfonyl, sulfoxide, heterocyclic, guanidine, ammonium, hydroxy, lower alkoxy, amino, or phenoxy;

$R_2$ is hydrogen, lower alkyl, lower alkenyl, lower alkynyl, aryl, heterocyclic (lower alkyl), or heterocyclic, each unsubstituted or substituted with at least one electron withdrawing substituent or at least one electron donating substituent; or $R_2$ is halogen or nitrogen, oxygen or sulfur, each substituted with hydrogen, lower alkyl or aryl, said lower alkyl or aryl groups being substituted or unsubstituted;

$R_3$ is hydrogen, lower alkyl, lower alkenyl, lower alkynyl, aryl, heterocyclic (lower alkyl), or heterocyclic, each unsubstituted or substituted with at least one electron withdrawing substituent or at least one electron donating substituent; or $R_3$ is halogen, or oxygen, nitrogen, or sulfur, each substituted with hydrogen, lower alkyl or aryl, said lower alkyl or aryl groups being substituted or unsubstituted, and n is 1–4.

4. The method of claim 1 wherein one of $R_2$ or $R_3$ is other than hydrogen.

5. The method of claim 1 wherein n is 1.

6. The method of claim 1 wherein n is 1; and one of $R_2$ and $R_3$ is hydrogen and the other is heterocyclic or (lower alkyl) heterocyclic.

7. The method of claim 1 wherein n is 1; and one of $R_2$ and $R_3$ is hydrogen and the other is (lower alkoxy) lower alkyl.

8. The method of claim 6 wherein one of $R_2$ and $R_3$ is hydrogen and the other is thienyl, furyl, pyrrolyl or phenyl.

9. The method of claim 1 wherein one of $R_2$ and $R_3$ is hydrogen and the other is lower alkenyl or lower alkynyl.

10. The method of claim 1 wherein one of $R_2$ and $R_3$ is hydrogen and the other is lower alkoxy.

11. The method of claim 1 wherein one of $R_2$ and $R_3$ is hydrogen and the other is lower alkyl.

12. The method of claim 1 wherein a unit dosage form containing from about 5 to about 1000 mg of said compound is administered.

13. The method of claim 1 wherein $R_1$ is hydrogen, or $R_1$ is methyl, ethyl, propyl, isopropyl, butyl, isobutyl, tertiary butyl, amyl or hexyl, unsubstituted or substituted with at least one electron withdrawing substituent or at least one electron donating substituent.

14. The method of claim 13 wherein $R_1$ is methyl.

15. The method of claim 1 wherein R is benzyl, unsubstituted or substituted with at least one electron withdrawing substituent or at least one electron donating substituent.

16. The method of claim 1 wherein the electron withdrawing substituent is halo, nitro, acyl, carboxyl, carboalkoxy, carboxamide, cyano, sulfonyl, sulfinyl, heterocyclic, guanidine or quaternary ammonium.

17. The method of claim 1 wherein the electron donating substituent is hydroxy, lower alkoxy, lower alkyl, amino or phenoxy.

18. The method of claim 1 wherein R is benzyl, $R_1$ is methyl, $R_2$ is hydrogen, $R_3$ is methyl and n is 1.

19. The method of claim 1 wherein R is benzyl, $R_1$ is methyl, $R_2$ is hydrogen, $R_3$ is phenyl and n is 1 and said compound is the D or L stereoisomer.

20. The method of claim 1 wherein R is benzyl, $R_1$ is methyl, $R_2$ is hydrogen, $R_3$ is (lower alkoxy) lower alkyl, and n is 1.

21. The method of claim 1 wherein R is benzyl, $R_1$ is methyl, $R_2$ is hydrogen, $R_3$ is methoxymethyl, and n is 1 and said compound is the D or L stereoisomer;

R is benzyl, $R_1$ is t-butyl, $R_2$ is hydrogen, $R_3$ is methyl and n is 1 and said compound is the D or L stereoisomer;

R is benzyl, $R_1$ is methyl, $R_2$ is hydrogen, $R_3$ is (2-thiomethyl)ethyl and n is 1 and said compound is the D or L stereoisomer;

R is (3-fluoro)benzyl, $R_1$ is methyl, $R_2$ is hydrogen, $R_3$ is methyl and n is 1 and said compound is the D or L stereoisomer;

R is (3-methoxy)benzyl, $R_1$ is methyl, $R_2$ is hydrogen, $R_3$ is methyl and n is 1 and said compound is the D or L stereoisomer;

R is benzyl, $R_1$ is methyl, $R_2$ is (3-thienyl), $R_3$ is hydrogen and n is 1 and said compound is the D or L stereoisomer;

R is benzyl, $R_1$ is methyl, $R_2$ is (2-thienyl), $R_3$ is hydrogen and n is 1 and said compound is the D or L stereoisomer;

R is benzyl, $R_1$ is methyl, $R_2$ is (2-furyl), $R_3$ is hydrogen and n is 1 and said compound is the D or L stereoisomer;

R is benzyl, $R_1$ is methyl, $R_2$ is (2-pyrrolyl), $R_3$ is hydrogen and n is 1 and said compound is the D or L stereoisomer;

R is benzyl, $R_1$ is methyl, $R_2$ is ethoxy, $R_3$ is hydrogen and n is 1 and said compound is the D or L stereoisomer; or R is benzyl, $R_1$ is methyl, $R_2$ is methoxy, $R_3$ is hydrogen and n is 1 and said compound is the D or L stereoisomer.

22. The method of claim 1 wherein the compound is the D stereoisomer.

23. The method of claim 1 wherein the compound is administered in combination with a pharmaceutically acceptable carrier.

24. The method of claim 23 wherein the compound is administered orally.

25. The method of claim 23 wherein the compound is administered intrathecally.

26. The method of claim 23 wherein the compound is administered intravenously.

27. The method of claim 23 wherein the compound is administered by inhalation or insufflation.

28. The method of claim 1 wherein $R_2$ is hydrogen; and $R_3$ is 2-furyl, 2-pyrrolyl, 1-pyrazolyl, 2-oxazolyl, 2-thiazolyl, pyridyl, pyrazinyl, or pyrimidinyl.

29. The method of claim 1 wherein $R_2$ is hydrogen; $R_3$ is $NR_4OR_5$; $R_4$ is hydrogen or lower alkyl; and $R_5$ is lower alkyl.

30. The method of claim 1 wherein R is benzyl, substituted with at least one electron withdrawing substituent or at least one electron donating substituent.

31. The method of claim 1 wherein the compound is (R)-N-benzyl-2-acetamido-3-methoxypropionamide, or a pharmaceutically acceptable salt thereof.

* * * * *